(12) United States Patent
Ingram et al.

(10) Patent No.: US 12,233,231 B2
(45) Date of Patent: Feb. 25, 2025

(54) VENTED CONNECTOR FOR MEDICAL FLUID VESSELS AND TAPERED PLUG

(71) Applicant: Avent, Inc., Alpharetta, GA (US)

(72) Inventors: Aaron N. Ingram, Canton, GA (US); Benjamin Martin Davis, Woodstock, GA (US); Mark M. Costello, County Mayo (IE); David A. Doornbos, Woodstock, GA (US); John Burke, Galway City (IE)

(73) Assignee: Avent, Inc., Alpharetta, GA (US)

( * ) Notice: Subject to any disclaimer, the term of this patent is extended or adjusted under 35 U.S.C. 154(b) by 51 days.

(21) Appl. No.: 17/743,558

(22) Filed: May 13, 2022

(65) Prior Publication Data
US 2022/0265987 A1    Aug. 25, 2022

Related U.S. Application Data

(63) Continuation of application No. 16/001,282, filed on Jun. 6, 2018, now Pat. No. 11,357,964, which is a (Continued)

(51) Int. Cl.
*A61M 39/20* (2006.01)
*A61J 15/00* (2006.01)
*A61M 39/10* (2006.01)

(52) U.S. Cl.
CPC .......... *A61M 39/20* (2013.01); *A61J 15/0026* (2013.01); *A61M 39/10* (2013.01); *A61M 2039/205* (2013.01)

(58) Field of Classification Search
CPC ...... A61M 39/02; A61M 39/10; A61M 39/20; A61M 2039/0202; A61M 2039/0205;
(Continued)

(56) References Cited

U.S. PATENT DOCUMENTS 2,872,060 A    2/1959  Brune et al.
3,057,502 A    10/1962 Wood
(Continued)

FOREIGN PATENT DOCUMENTS

CA    2167572 A1    2/1995
CA    2379187 A1    2/2001
(Continued)

OTHER PUBLICATIONS

Canadian Examiner's Report for CA 2,959,393; Jun. 4, 2018; 4 pgs.
(Continued)

*Primary Examiner* — Kami A Bosworth
(74) *Attorney, Agent, or Firm* — Meunier Carlin & Curfman LLC

(57) ABSTRACT

A connector for medical fluid vessels includes a fluid-seal fitting such as a male plug defining a lumen and mating with a cooperating connector, a mechanical fastener such as a screw thread for mating with the cooperating connector, and an outer housing positioned around the plug to form an annular space. A cap can be provided with a fluid-seal fitting such as a male plug for mating with the lumen of the connector. In example embodiments, the male plug is tapered and can comprise one or more projections for sealingly engaging with the lumen of the connector. According to some example embodiments, the cap can be tethered to the connector.

17 Claims, 11 Drawing Sheets

Related U.S. Application Data continuation-in-part of application No. 14/844,956, filed on Sep. 3, 2015, now Pat. No. 10,668,263.

(60) Provisional application No. 62/515,880, filed on Jun. 6, 2017, provisional application No. 62/192,614, filed on Jul. 15, 2015, provisional application No. 62/047,389, filed on Sep. 8, 2014.

(58) Field of Classification Search
CPC ...... A61M 2039/1094; A61M 2039/205; A61J 15/0096; B65D 51/16; B65D 51/1605; B65D 51/1611; B65D 2205/02; B65D 2205/025; B65D 51/1622

See application file for complete search history.

(56) References Cited

U.S. PATENT DOCUMENTS

| | | |
|---|---|---|
| 3,307,552 A | 3/1967 | Strawn |
| 3,339,772 A | 9/1967 | Miller |
| 3,716,163 A | 2/1973 | Marcel |
| 4,214,586 A | 7/1980 | Mericle |
| 4,230,231 A | 10/1980 | Burnett et al. |
| 4,237,935 A | 12/1980 | Demonte et al. |
| 4,349,024 A | 9/1982 | Ralston, Jr. |
| 4,416,273 A | 11/1983 | Grimes |
| 4,417,890 A | 11/1983 | Dennehey et al. |
| 4,573,602 A | 3/1986 | Goldberg |
| 4,597,758 A | 6/1986 | Aalto et al. |
| 4,904,238 A | 2/1990 | Williams |
| 4,963,132 A | 10/1990 | Gibson |
| 4,994,068 A | 2/1991 | Hufnagle |
| 5,184,742 A | 2/1993 | DeCaprio et al. |
| 5,385,372 A | 1/1995 | Utterberg |
| 5,401,255 A | 3/1995 | Sutherland et al. |
| 5,591,344 A | 1/1997 | Kenley et al. |
| 5,782,808 A | 7/1998 | Folden |
| 5,813,554 A | 9/1998 | Marangoni Graziani et al. |
| 5,830,195 A | 11/1998 | Peters et al. |
| 5,857,580 A | 1/1999 | Iidaka |
| 5,881,774 A | 3/1999 | Utterberg |
| 5,951,519 A | 9/1999 | Utterberg |
| 6,183,465 B1 | 2/2001 | Meier et al. |
| D463,546 S | 9/2002 | Jansen et al. |
| 6,447,480 B1 | 9/2002 | Brunel |
| D473,646 S | 4/2003 | Baillargeon et al. |
| 6,632,199 B1* | 10/2003 | Tucker ................ A61M 5/3134 604/192 |
| 6,808,521 B1 | 10/2004 | McMichael |
| 6,883,778 B1 | 4/2005 | Newton et al. |
| 7,077,829 B2 | 7/2006 | McGuckin, Jr. et al. |
| 7,080,672 B2 | 7/2006 | Fournie et al. |
| 7,578,803 B2 | 8/2009 | Rome et al. |
| 7,628,782 B2 | 12/2009 | Adair et al. |
| 7,658,734 B2 | 2/2010 | Adair et al. |
| 7,686,823 B2 | 3/2010 | Pingleton et al. |
| 7,988,683 B2 | 8/2011 | Adair et al. |
| 8,066,670 B2 | 11/2011 | Cluff et al. |
| D665,497 S | 8/2012 | Marshall et al. |
| 8,333,693 B2 | 12/2012 | Hamazaki |
| 8,491,535 B2 | 7/2013 | Limaye |
| 8,506,549 B2 | 8/2013 | Breuer-Thal et al. |
| 8,652,104 B2 | 2/2014 | Goral et al. |
| 8,852,168 B2 | 10/2014 | Barron et al. |
| 8,915,883 B2 | 12/2014 | Baid |
| 8,932,264 B2 | 1/2015 | DeSalvo |
| D736,906 S | 8/2015 | Schultz |
| D737,436 S | 8/2015 | Lev et al. |
| 9,308,362 B2 | 4/2016 | Mansour et al. |
| 9,399,116 B2 | 7/2016 | Goral et al. |
| 9,579,452 B2 | 2/2017 | Adair et al. |
| 9,604,046 B2* | 3/2017 | Steele .................. A61M 39/20 |
| 9,814,871 B2 | 11/2017 | Wlodarczyk et al. |
| 9,895,526 B2 | 2/2018 | Korogi et al. |
| 10,420,709 B2 | 9/2019 | Davis et al. |
| 2002/0173748 A1 | 11/2002 | McConnell et al. |
| 2003/0032940 A1 | 2/2003 | Doyle |
| 2004/0168690 A1 | 9/2004 | Payne |
| 2004/0211484 A1 | 10/2004 | Fournie |
| 2004/0238776 A1 | 12/2004 | Peters et al. |
| 2005/0124935 A1 | 6/2005 | McMichael |
| 2005/0261664 A1 | 11/2005 | Rome et al. |
| 2006/0060202 A1 | 3/2006 | Flynn et al. |
| 2006/0161115 A1 | 7/2006 | Fangrow |
| 2008/0103486 A1 | 5/2008 | Owens |
| 2008/0128646 A1 | 6/2008 | Clawson |
| 2008/0183153 A1 | 7/2008 | Enns |
| 2008/0200904 A1 | 8/2008 | Cluff et al. |
| 2009/0182309 A1* | 7/2009 | Muffly ................ A61M 39/165 604/535 |
| 2010/0292673 A1 | 11/2010 | Korogi et al. |
| 2011/0044850 A1 | 2/2011 | Solomon et al. |
| 2011/0144481 A1 | 6/2011 | Feer et al. |
| 2011/0240162 A1 | 10/2011 | Zeyfang |
| 2011/0270230 A1 | 11/2011 | Sag et al. |
| 2012/0022457 A1* | 1/2012 | Silver ................ A61M 39/1011 604/187 |
| 2012/0029481 A1 | 2/2012 | Pech et al. |
| 2012/0191029 A1 | 7/2012 | Hopf et al. |
| 2012/0302997 A1* | 11/2012 | Gardner ................ A61M 39/20 604/533 |
| 2012/0323221 A1 | 12/2012 | Gallo et al. |
| 2013/0079730 A1 | 3/2013 | Mosler et al. |
| 2013/0103002 A1 | 4/2013 | Fruenlund et al. |
| 2014/0261758 A1 | 9/2014 | Wlodarczyk et al. |
| 2014/0276458 A1 | 9/2014 | Mansour et al. |
| 2014/0276652 A1 | 9/2014 | Gittard |
| 2015/0005716 A1 | 1/2015 | Adair et al. |
| 2015/0297839 A1 | 10/2015 | Sanders et al. |
| 2016/0067471 A1 | 3/2016 | Ingram et al. |
| 2016/0089528 A1 | 3/2016 | Schuessler |
| 2016/0151584 A1* | 6/2016 | Deleuil ................. A61M 5/344 604/263 |
| 2016/0206516 A1 | 7/2016 | Kunishige et al. |
| 2016/0296724 A1 | 10/2016 | Goral et al. |
| 2016/0317393 A1 | 11/2016 | Davis et al. |
| 2018/0071169 A1 | 3/2018 | Davis et al. |

FOREIGN PATENT DOCUMENTS

| | | |
|---|---|---|
| EP | 0453 264 A1 | 10/1991 |
| EP | 2 583 715 A1 | 4/2013 |
| GB | 2 453 361 A | 4/2009 |
| JP | A09000618 | 9/1997 |
| JP | 2008518719 A | 6/2008 |
| WO | 99/64103 A1 | 12/1999 |
| WO | WO 2006/052655 A2 | 5/2006 |
| WO | WO 2011/066586 A1 | 6/2011 |

OTHER PUBLICATIONS

ENFit Female Connector; 1 pg; date unknown.
ENFit Male Connector; 1 pg; date unknown.
English Translation of Japanese Office Action for JP Ap. No. 2017-531979; Mar. 27, 2018; 4 pgs.
International Search Report & Written Opinion for PCT/US2015/048382; Nov. 5, 2015; 11 pgs.
ISO 80369-3, Small Bore Enteral Connector Standards; 3 pgs; Jul. 21, 2014.
New ISO Tubing Connector Standards: A Follow-Up to the Sentinel Event Alert Webinar PowerPoint Presentation; www.ointcommission.org; 50 pgs; Dec. 3, 2014.
New Tube Feeding Connectors Webinar PowerPoint Presentation; www.oley.org; 24 pgs; Jun. 24, 2014.
StayConnected2014 Informational Bracelet; 1 pg; date unknown.
http://www.stayconnected2014.org/get-ready.html; 1 pg; date unknown.
International Application No. PCT/US2018/051248, International Search Report and Written Opinion mailed on Mar. 13, 2019, 11 pages.

* cited by examiner

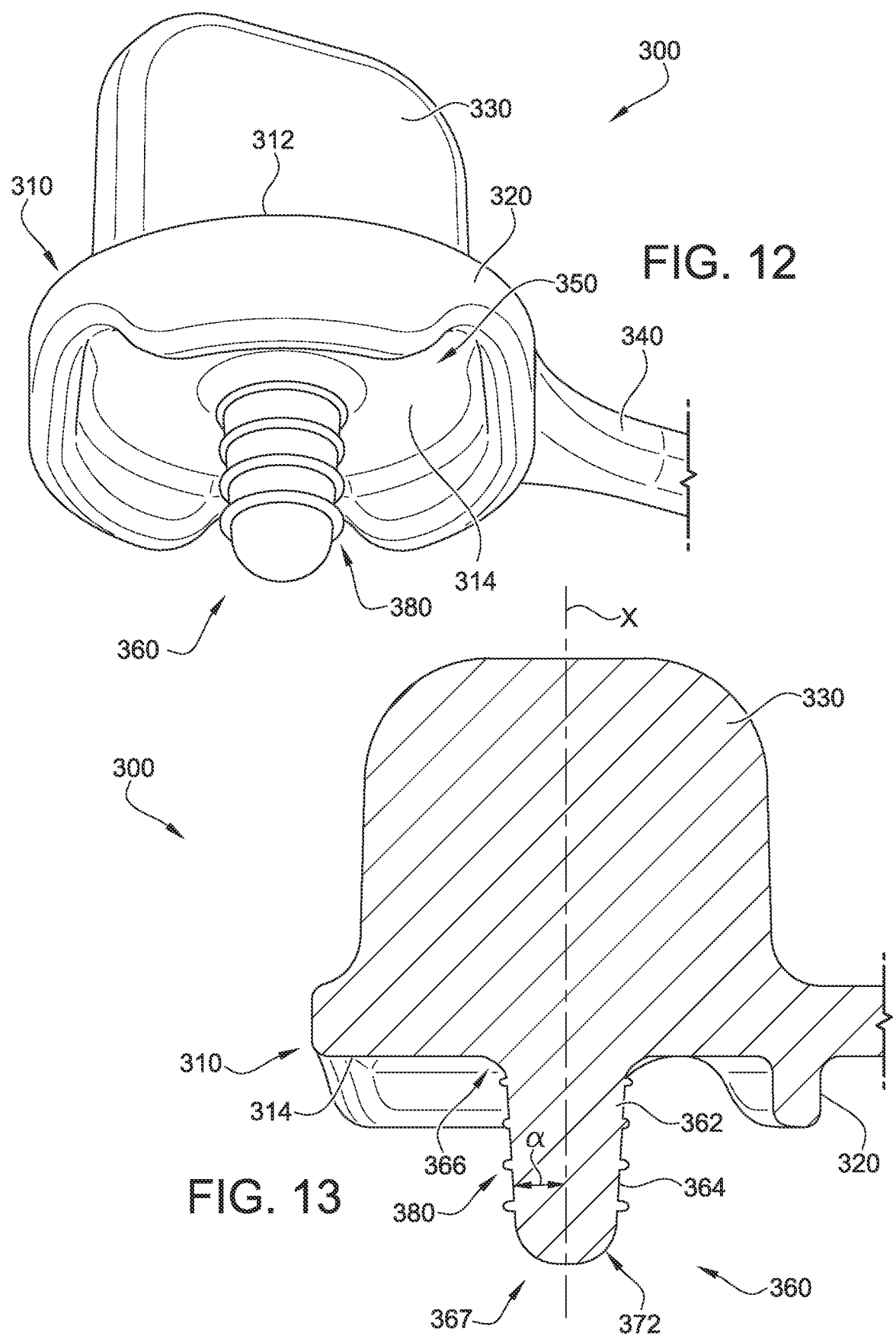

VENTED CONNECTOR FOR MEDICAL FLUID VESSELS AND TAPERED PLUG

CROSS-REFERENCE TO RELATED APPLICATIONS

This application is a continuation of U.S. patent application Ser. No. 16/001,282 filed Jun. 8, 2018, issued as U.S. Pat. No. 11,357,964 on Jun. 14, 2022, which claims the priority benefit of U.S. Provisional Patent Application Ser. No. 62/515,880 filed Jun. 6, 2017, and is a continuation-in-part of U.S. Non-Provisional patent application Ser. No. 14/844,956 filed Sep. 3, 2015, which claims the priority benefit of U.S. Provisional Patent Application Ser. No. 62/047,389 filed Sep. 8, 2014 and U.S. Provisional Patent Application Ser. No. 62/192,614 filed Jul. 15, 2015, the entireties of which are hereby incorporated herein by reference for all purposes.

TECHNICAL FIELD

The present invention relates generally to medical devices, and more particularly to connectors for vessels for fluids in the medical field, and to tethered capping plugs for sealing engaging with connectors for vessels for fluids.

BACKGROUND

Healthcare patients are commonly given fluids such as medication and nutrients by being connected to fluid-delivery systems via fluid vessels. Common fluid vessels for delivering such fluids include small-bore tubes and catheters. A problem arises when these fluid tubes are misconnected. That is, when a tube from one fluid delivery system is connected to a tube intended for connection to another fluid delivery system that serves a completely different function, for example, when a feeding administration set is inadvertently connected to a tracheostomy tube. Such tubing misconnections are also referred to as LUER misconnections, small-bore misconnections, and/or wrong-route errors. Tubing misconnections have resulted in patient injuries and/or deaths, and are widely recognized as underreported.

An underlying cause of these misconnections has been attributed to the universal design of LUER connectors, which are one of the most commonly used types of small-bore connectors in healthcare. These connectors are used to couple the tubing of one medical device to another. However, the simple design and ease of use of LUER connectors allows the tube of the device of one delivery system to be connected to a tube of an unrelated system that has a different intended use (e.g., vascular, enteral, respiratory, epidural, or intrathecal), resulting in healthcare providers inadvertently connecting wrong systems together and thereby causing liquids (e.g., medications or enteral feedings) or gases (e.g., oxygen) to be delivered through the wrong route.

Efforts are underway to develop standards, such as the ISO 80369 standards, for tubing connections. These standards hold the promise of significantly addressing the tubing-misconnection problem. For example, these standards provide for a new connector for enteral feeding tubes that prevents misconnection to non-enteral connectors. This new enteral-only tube connector is also referred to as the ENFIT connector.

Yet there remain other opportunities for improving these and other connectors. For example, the new ENFIT connector for enteral feeding tubes includes an outer housing that could retain feeding liquids and thereby allow for bacteria colonization. This can result in unsanitary conditions that can inadvertently contaminate feeding fluids later delivered to the patient through the degraded ENFIT connector.

Accordingly, it can be seen that needs exist for improved connectors for fluid tubes to reduce the risk of bacteria colonization. It is to the provision of solutions to this and other needs that the present invention is primarily directed.

SUMMARY

In example embodiments, the present invention relates to individual connectors as well as connector-sets (of individual connectors) for coupling together two medical-fluid vessels. The connectors and connector-sets advantageously provide for drainage and air-drying of any residual fluid that might otherwise be retained and result in bacteria colonization, as well as for breaking a vacuum to prevent fluid backflow and thus ensure more accurate dosing.

In one aspect, the present invention relates to a connector that includes a fluid-seal fitting such as a male plug for mating with a cooperating connector, a mechanical fastener such as a screw thread for mating with the cooperating connector, and an outer housing positioned around the plug to form an annular space. The connector outer housing includes one or more vent openings for drainage and air-drying of any residual fluid in the annular space when the cap is plugged on. For example, the connector vent openings can be in an endwall of the outer housing, a peripheral sidewall of the outer housing, or both.

In another aspect, the invention relates to a sanitary cap that includes a fluid-seal fitting such as a male plug for mating with a lumen of the connector plug. The cap includes one or more vent openings for drainage and air-drying of any residual fluid in the annular space when the cap is plugged on. For example, the cap vent openings can be in an endwall body of the cap, a peripheral sidewall of the cap, or both. In some embodiments in which the cap vent openings are in the cap sidewall, they are formed by notches or recesses between segments of the cap sidewall, and in these or other similar embodiments mechanical stop surfaces are provided on the cap and the connector to limit to travel of the cap sidewall relative to the outer-housing sidewall to ensure that the cap vents remain open for ventilation.

In another aspect, the invention relates to a fluid-seal fitting such as a male plug for mating with a cooperating connector. The male plug can be tapered and comprise one or more projections formed on an outer periphery portion thereof for providing an interference with a lumen of the connector. In one example embodiment, the plug comprises about four spaced-apart ribs. In example embodiments, each rib generally extends around the entire periphery of the plug.

In another aspect, the invention relates to a cap for sealing with a lumen of a male connector. In example embodiments, the cap includes a body having an upper surface and a lower surface. The upper surface includes a handle extending therefrom and the lower surface includes a plug extending therefrom. The plug has a first end engaged with the lower surface and a second end axially extending therefrom. In example embodiments, the plug includes at least one projection extending therefrom for sealing engagement with the lumen of the male connector.

In example embodiments, the plug comprises an elongate body and an outer peripheral surface, and wherein the plug tapers from the first end to the second end. In example embodiments, the plug comprises a length of about 5 millimeters.

In example embodiments, the at least one projection has a rib-like ring projecting around the entire periphery of the outer peripheral surface of the plug body, and wherein an outer surface of the rib-like ring is configured for providing an interference fit with an internal surface of the lumen of the male connector. According to some example embodiments, the plug includes two or more projections. According to one example embodiment, the plug includes four spaced-apart projections, each of the projections extending around the entire periphery of the plug. In example embodiments, the at least one projection has an outer diameter of between about 3.0-3.5 millimeters and wherein the internal diameter of the lumen is about 2.90 millimeters. In example embodiments, at least between about 0.040-0.180 millimeters of interference is provided between the at least one projection and the interior surface of the lumen. In example embodiments, the projections and interference with the lumen is such that a removal force of between about 2.5-15 N is required to remove the fully-inserted plug from the lumen. In example embodiments, a first projection is spaced about 1.389 millimeters from the second end, a second projection is spaced about 2.392 millimeters from the second end, a third projection is spaced about 3.392 millimeters from the second end, and a fourth projection is spaced about 4.392 millimeters from the second end. In example embodiments, the first projection has an outer diameter of about 3.024 millimeters, the second projection has an outer diameter of about 3.034 millimeters, the third projection has an outer diameter of about 3.051 millimeters, and the fourth projection has an outer diameter of about 3.2 millimeters. In example embodiments, the cap further includes a tether for tethering the cap to the male connector.

In yet another aspect, the invention relates to a connector for connection to a fluid vessel and a cooperating connector, the connector including a first end from which the vessel extends, a second end, and a lumen extending therethrough from the first end to the second end; a fluid-seal fitting that at least partially defines the lumen and sealingly mates with the cooperating connector to provide conveyance of the fluid; an outer housing positioned around the fluid-seal fitting to form an annular space therebetween with an access opening at the second end of the connector; and a cap repositionable between a plugged position capping the connector second end and an unplugged position not capping the connector second end, the cap including one or more vent openings extending between the annular space and external to the annular space when the cap is in the plugged position capping the access opening of the annular space, wherein the one or more cap vent openings allow for drainage and air-drying of any residual amount of the fluid in the annular space, and wherein the cap further comprises a plug for providing sealed engagement with the lumen, the tapered plug comprising at least one projection extending around the outer periphery of the plug, the at least one projection providing for an interference fit with an interior surface of the lumen.

In example embodiments, the plug includes an elongate body and an outer peripheral surface, and wherein the plug tapers from the first end to the second end. In example embodiments, the plug has a length of about 5 millimeters. In example embodiments, the at least one projection has a rib-like ring projecting around the entire periphery of the outer peripheral surface of the plug body, and wherein an outer surface of the rib-like ring is configured for providing an interference fit with an internal surface of the lumen of the male connector. In example embodiments, the plug includes two or more projections. In example embodiments, the plug includes four spaced-apart projections, each of the projections extending around the entire periphery of the plug.

In example embodiments, the at least one projection has an outer diameter of between about 3.0-3.5 millimeters and wherein the internal diameter of the lumen is about 2.90 millimeters. In example embodiments, at least between about 0.040-0.180 millimeters of interference is provided between the at least one projection and the interior surface of the lumen. In example embodiments, the projections and interference with the lumen is such that a removal force of between about 2.5-15 N is required to remove the fully-inserted plug from the lumen. In example embodiments, a first projection is spaced about 1.389 millimeters from the second end, a second projection is spaced about 2.392 millimeters from the second end, a third projection is spaced about 3.392 millimeters from the second end, and a fourth projection is spaced about 4.392 millimeters from the second end. In example embodiments, the first projection includes an outer diameter of about 3.024 millimeters, the second projection includes an outer diameter of about 3.034 millimeters, the third projection includes an outer diameter of about 3.051 millimeters, and the fourth projection includes an outer diameter of about 3.2 millimeters. In example embodiments, at least a portion of the lumen includes a recessed portion or annular undercut defined therein configured for receiving the at least one projection of the plug of the cap.

These and other aspects, features, and advantages of the invention will be understood with reference to the drawing figures and detailed description herein, and will be realized by means of the various elements and combinations particularly pointed out in the appended claims. It is to be understood that both the foregoing general summary description and the following brief description of the drawings and detailed description of example embodiments are exemplary and explanatory of preferred embodiments of the invention, and are not restrictive of the invention, as claimed.

BRIEF DESCRIPTION OF THE DRAWINGS

FIG. 12 shows a perspective view of a tethered plug for sealingly engaging with the lumen of the connector according to another example embodiment of the present invention, the plug having one or more projections provided thereon.

FIG. 13 is a cross-sectional view of the tethered plug of FIG. 12.

DETAILED DESCRIPTION OF EXAMPLE EMBODIMENTS

Figure 1:
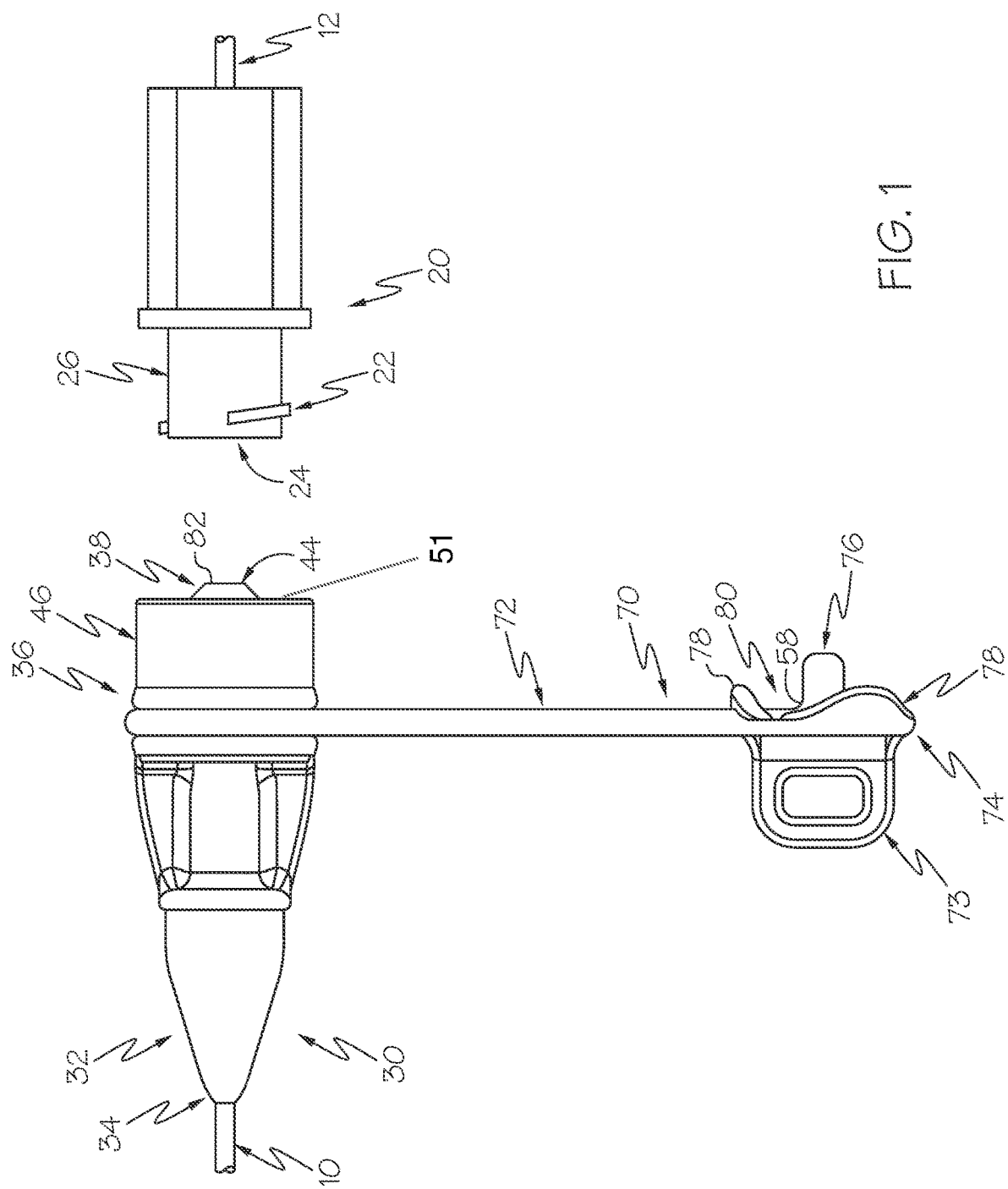
FIG. 1 is a side view of a vented male connector according to a first example embodiment of the present invention, shown with a mating female connector and with its cap unplugged so that it's ready for connection to the mating female connector.
Figure 3:
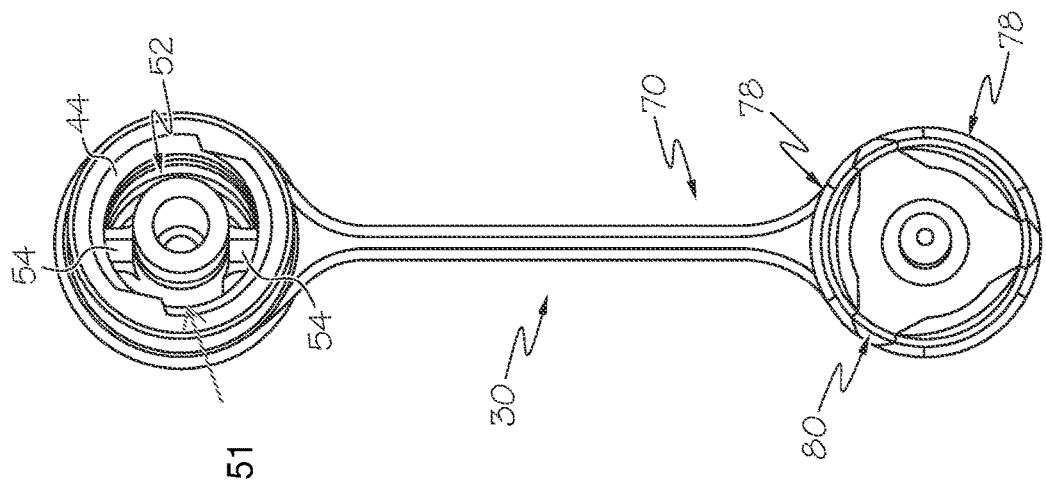
FIG. 3 is another front perspective view of the male connector of FIG. 1.
Figure 2:
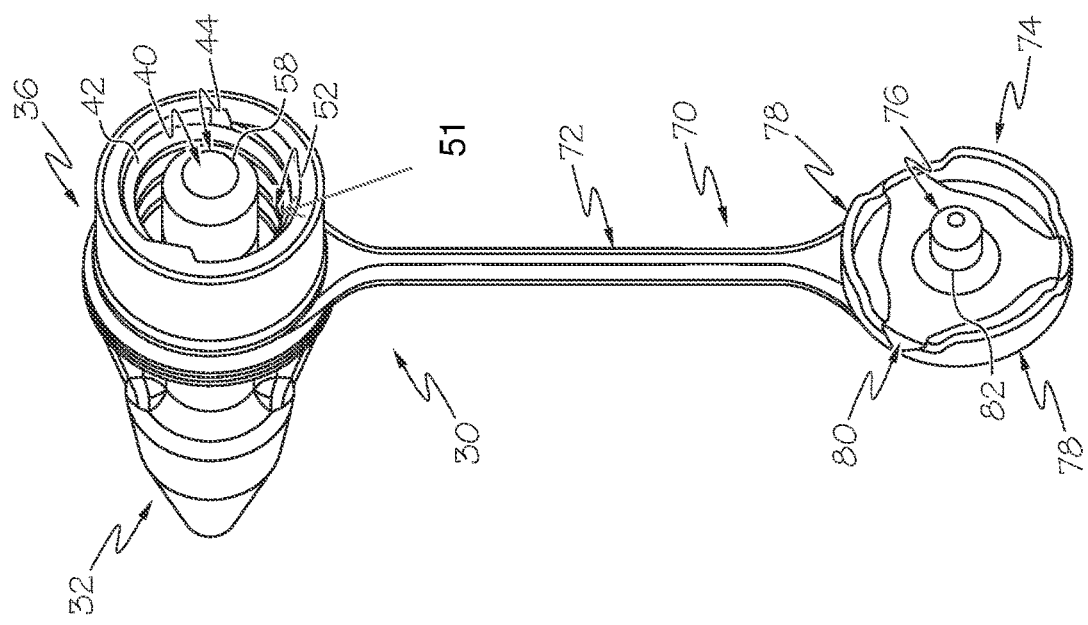
FIG. 2 is a front perspective view of the male connector of FIG. 1.
Figure 5:
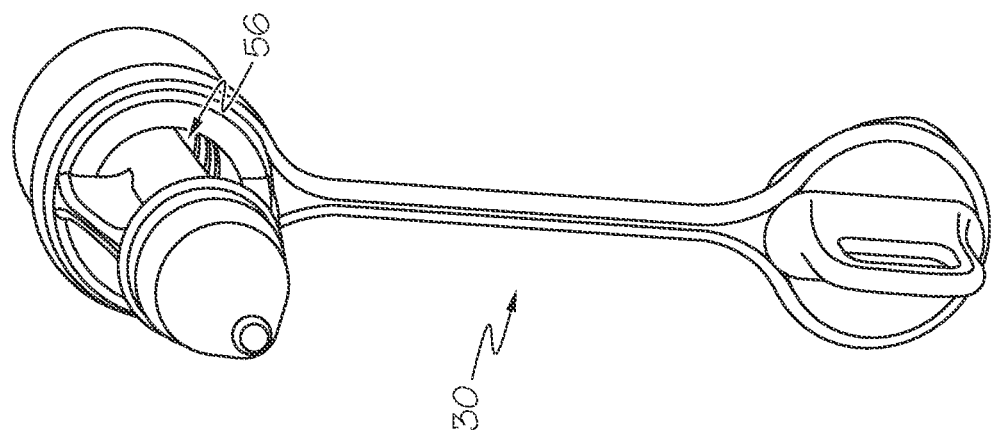
FIG. 5 is another rear perspective view of the male connector of FIG. 1.
Figure 4:
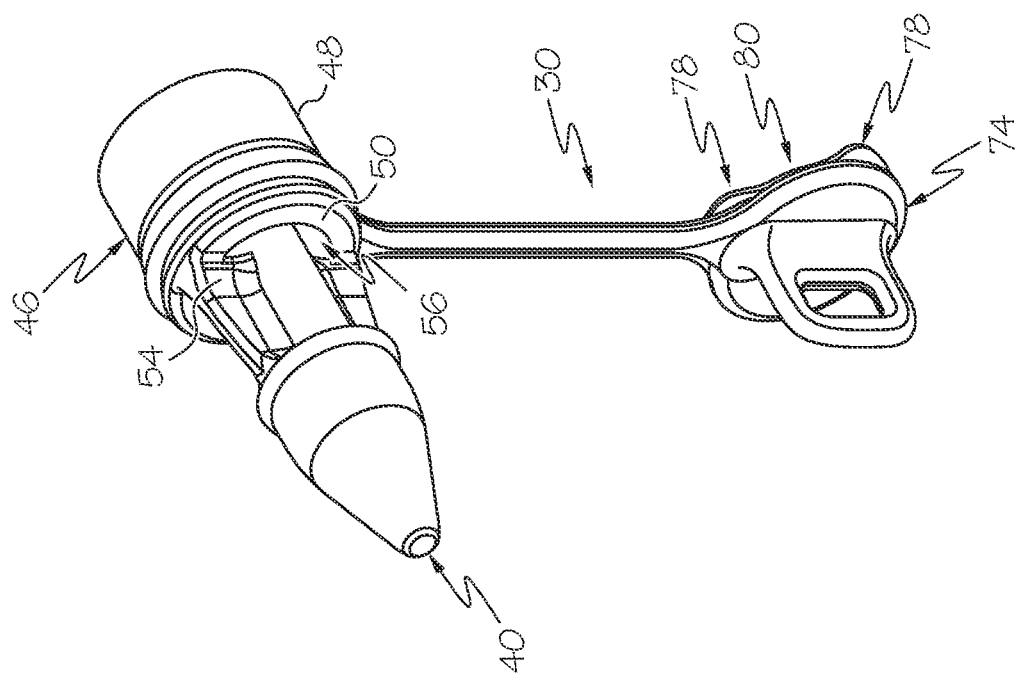
FIG. 4 is a rear perspective view of the male connector of FIG. 1.
Figure 7:
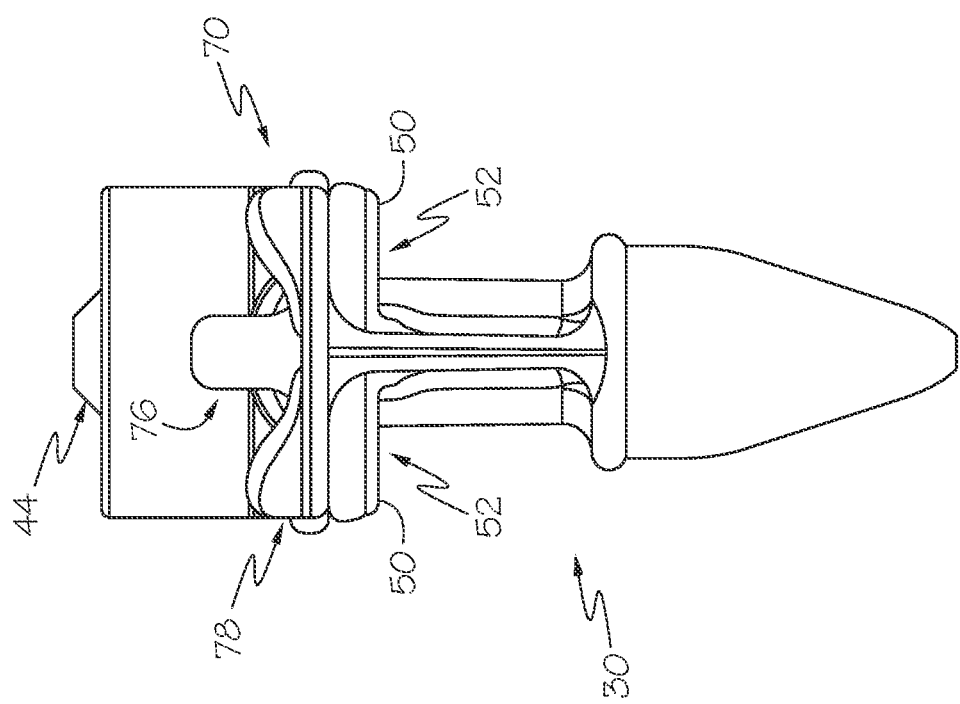
FIG. 7 is another side view of the male connector of FIG. 1.
Figure 6:
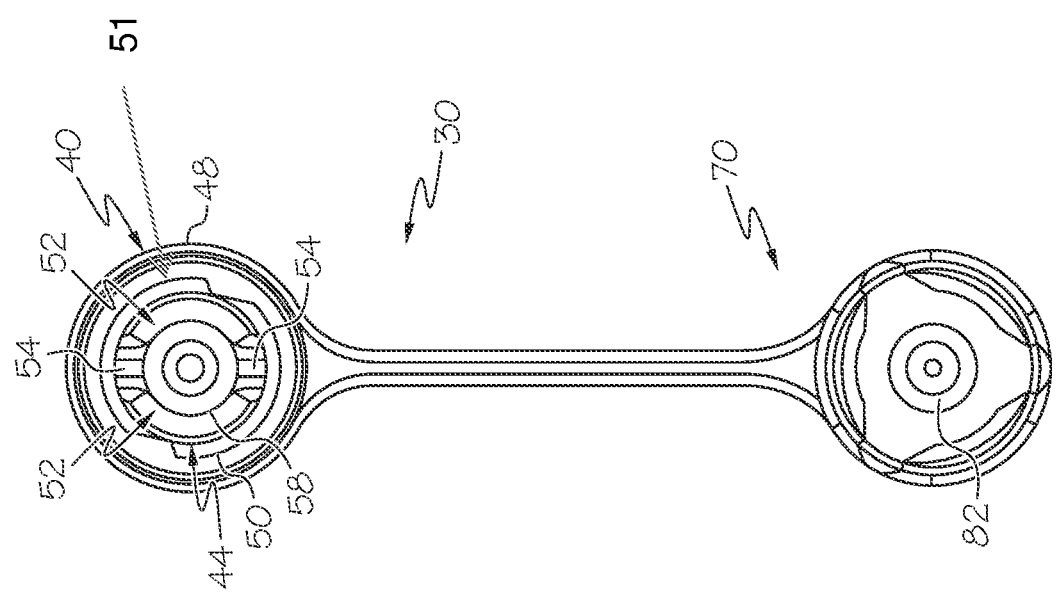
FIG. 6 is a front view of the male connector of FIG. 1.
Figure 8:
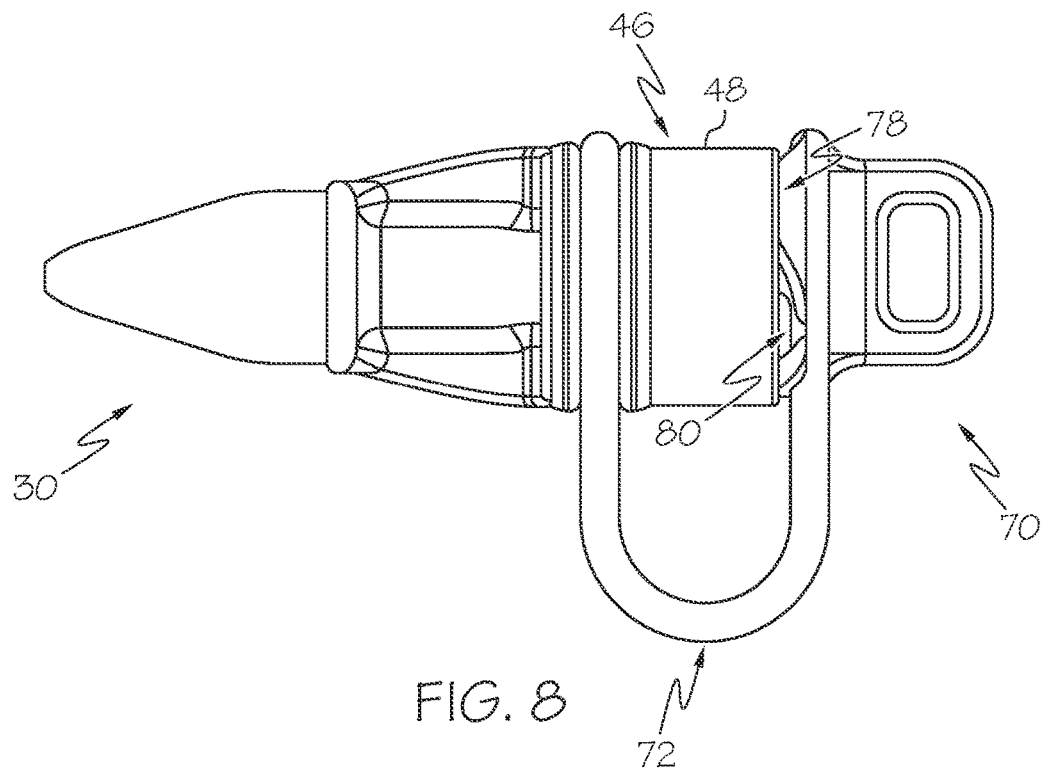
FIG. 8 shows the male connector of FIG. 1 with its cap in a plugged position.
Figure 9:
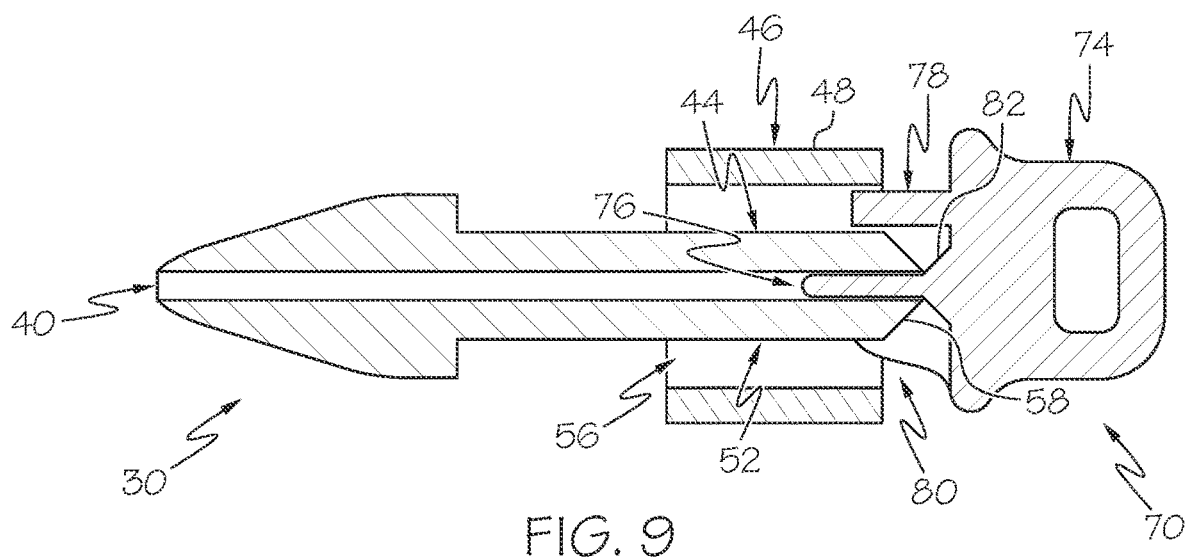
FIG. 9 is a cross-sectional view of the male connector of FIG. 8 showing a ventilation passageway for airflow through the connector with its cap in a plugged position.

The present invention may be understood more readily by reference to the following detailed description taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-9 show a vented connector 30 according to a first example embodiment of the invention. The connector 30 attaches to a medical fluid vessel 10 and mates with a cooperating connector 20 attached to an inline medical fluid vessel 12, with the connectors collectively forming a connector-set or coupling that detachably couples the vessels together for fluid flow therethrough. The connectors 20 and 30 can be made of conventional materials (e.g., as silicone or polyurethane) by conventional fabrication techniques and equipment (e.g., molding).

In the depicted embodiment, the vented connector 30 is attached to a vessel 10 that is a tube, though the term "vessel" is intended to be broadly construed to include any carrier or container for a fluid as well as any fluid-delivery device, and as such in other embodiments the vessel is a catheter, hose, bottle, bag, syringe, pump, or the like. As such, the connectors 20 and 30 can be used to couple together two vessels (with one vessel in/at the patient and the other vessel connected to an upstream medical fluid-delivery device such as a syringe) or to couple one vessel to a medical device (with one vessel in/at the patient and the other vessel being or a part of an upstream medical fluid-delivery device such as a syringe). In the depicted embodiment, the vented connector 30 is used for a vessel 10 for enteral feeding, with the term "vessel" in the "enteral feeding" context intended to be broadly construed to include not just feeding bags but also breast pumps, food bottles, other food-storage containers, extension sets, and the like. In the depicted embodiment, the vented connector 30 is an ENFIT connector for enteral feeding tubes, though in other embodiments the innovative features are included in connectors for fluid vessels for non-enteral and/or non-small-bore (medical or other) applications. And in the depicted embodiment, the vented connector 30 is a male connector and the cooperating connector 20 is a mating female connector, though in other embodiments this is reversed to provide a vented and/or capped female connector with an outer housing defining an annular space. In addition, the vented connector 30 is described herein for use with fluids, which as used herein means liquids and gases.

The connector 30 includes a vessel-attaching portion 32 defining a rear end 34, a coupling-attaching portion 36 defining a front end 38, and a lumen 40 extending longitudinally therethrough from end to end. The vessel-attaching portion 32 attaches to (e.g., receives and secures) the vessel 10 and secures it in place with a good seal by conventional structures such as crimps or adhesives so that the vessel extends longitudinally from the rear end 34. The coupling-attaching portion 36 and the cooperating connector 20 detachably couple together mechanically by mating attachment fittings such as the depicted screw threads 42 and 22 (of the connector 30 and the cooperating connector 20, respectively) or other conventional mating mechanical fasteners as are known to persons of ordinary skill in the art such as bayonet fitting, snap-fit couplings, and the like. And the coupling-attaching portion 36 and the cooperating connector 20 sealingly mate together for fluid conveyance by mating male and female fittings such as the depicted male plug 44 and female receptacle 24 (of the connector 30 and the cooperating connector 20, respectively) or other conventional fluid-sealing structures as are known to persons of ordinary skill in the art such other friction fittings. In the depicted embodiment, the male plug 44 includes a peripheral wall that defines the lumen 40 extending axially all the way through it to convey the fluid through the connector 30. In some embodiments, the mating male and female seal fittings are designed to provide sufficient mechanical/frictional retention forces that the connectors 30 and 20 are securely coupled together and the connectors 30 and 20 thus do not include any separate screw threading or other mechanical fasteners.

In addition, the connector 30 includes an outer housing 46 surrounding its plug 44, for example including a peripheral sidewall 48 and an endwall 50. The outer-housing sidewall 48 is arranged coaxially with and surrounding the plug 44 thereby forming an annular space 52 therebetween with an access opening 51 at the front end 38 of the connector 30 (opposite the endwall). In this way, when the two connectors are coupled together with the male plug 44 of the connector 30 inserted into the female receptacle 24 of the cooperating connector 20, the peripheral sidewall or barrel 26 (defining the receptacle 24) of the cooperating connector 20 is coaxially received in the annular space 52 (between the outer-housing peripheral sidewall 48 and the plug 44) of the connector 30. And the connectors 30 and 20 can be coupled together by the screw threads 42 being inner threads on the outer-housing sidewall 48 and the mating threads 22 being outer threads on the receptacle sidewall 26, by mating threads between the plug and the receptacle sidewall, or by other threading arrangements. The outer-housing sidewall 48 of the connector 30 and the receptacle sidewall 26 of the cooperating connector 20 are typically generally cylindrical in shape and solid in structure (i.e., not fluid permeable).

The outer-housing endwall 50 extends at least partially between the outer-housing sidewall 48 and the plug 44, with at least one (e.g., two, as depicted) connecting portion 54 extending inwardly from the outer-housing sidewall to fix the outer-housing sidewall relative to the plug and thereby form the annular space 52. Typically each connecting portion 54 extends all the way between (e.g., radially, as depicted) and fixes together the outer-housing sidewall 48 and the plug 44. To provide for fluid drainage and airflow ventilation, the outer-housing endwall 50 of the connector 30 includes at least one (e.g., two, as depicted) vent openings 56 providing fluid communication between the annular space 52 and external to the annular space. The connector vent openings 56 can be in the form of two curved slots extending between two connecting portions 54 in the form of radial spokes, as depicted. Alternatively, the connector vent openings can be in the form of ports (e.g., holes in a circular, polygonal, frusto-conical, or other regular or irregular shape) extending axially through the endwall and/or radially through the outer sidewall, mesh openings in an endwall that is a mesh (e.g., a screen, grate, or lattice), or other types and arrangements of openings that provide for fluid drainage and airflow ventilation for the annular space. In addition, the outer-housing endwall 50 has an inner surface (partially defining the annular space 52) that can be sloped (ramped or taper, all or only part of it) toward the connector vent openings 56 to help direct fluid toward them.

In this way, any residual fluid from the vessels 10 and 12 that might otherwise be retained in the annular space 52 resulting in bacteria colonization will instead tend to drain out through the connector vent openings 56 and be dried by airflow in and/or out of the vent openings. Furthermore, the connector vent openings 56 in the outer-housing endwall 50 provide better access to the annular space 52 for inspection and cleaning. Moreover, when the connector 30 is disconnected from the cooperating connector 20, a vacuum can form in the lumen 40 and induce a backflow of the fluid into the connector 30 and/or the cooperating connector 20, resulting in dosing inaccuracies, and the connector vent openings 56 can function to assist in breaking the vacuum to prevent fluid backflow and thus provide for more accurate dosing.

In addition, the connector 30 optionally includes a sanitary cap 70 for the lumen 40 at its front end 38 (opposite the attachment of the vessel 10). The cap 70 can be attached to the connector 30 by a tether 72 such as an integral length of material (as shown) or a cord, string, band, chain, or the like. In addition, the cap 70 can include a handle 73 for gripping to move the cap between its unplugged (see FIGS. 1-7) and plugged positions (see FIGS. 8-9). In the plugged position the cap 70 seals off the lumen 40 and the vessel 10 from outside contamination, which can be advantageous for example in enteral feeding applications in which the vessel 10 is inserted into the patient and left there for future feedings.

The cap 70 includes a body or endwall 74 with a seal fitting (e.g., a plug) 76 and a peripheral sidewall 78 axially extending from it. The cap body/endwall 74 is typically a solid member such as a panel for sealing the annular space when capped. And the cap sidewall 78 can be a solid peripheral member such as a collar or flange, or two or more peripherally arranged prongs such as fingers or tabs, for reception and retention in the annular space when capped. In the plugged position, the cap plug 76 is received in the connector-plug lumen 40 at its front end 38 with a snug fit for sealing to prevent the escape of fluids from the vessel 10. And the cap sidewall 78 is received in the annular space 52 through its access opening 51 so that it engages the connector 30 with a snug fit for mechanical/frictional retention to removably secure the cap 70 in place in the plugged position. In other embodiments, the cap seal fitting is a sleeve, recess, or other structural element that mates with the connector seal fitting to seal the lumen closed. And in yet other embodiments, the cap 70 and the connector 30 additionally or alternatively include mating screw threads or other fasteners for removably securing the parts together.

To provide for fluid drainage and airflow ventilation of the annular space 52 when the cap 70 is the plugged position, the cap includes at least one (e.g., three, as depicted) vent openings 80 providing fluid communication between the annular space and external to the annular space. The cap vent openings 80 can be in the form of one or more notches defined by gaps between one or more segments of the cap sidewall 78, for example the three curved notches between the three segments of the cap sidewall formed by the undulating edge of the cap sidewall, as depicted. Alternatively, the cap vent openings can be in the form of ports (e.g., holes in a circular, polygonal, conical, or other regular or irregular shape) extending axially through the cap body/endwall and/or radially through the cap sidewall, mesh openings in a portion of the cap body that is a mesh (e.g., a screen, grate, or lattice), or other types and arrangements of openings that provide for fluid drainage and airflow ventilation for the annular space with the cap in the plugged position.

In this way, any residual fluid from the vessels 10 and 12 that might otherwise be retained in the annular space 52 (upon disconnection of the connectors 30 and 20) resulting in bacteria colonization will instead tend to drain out through the cap vent openings 80 and be dried by airflow in and/or out of the vent openings. Furthermore, the cap vent openings 80 can facilitate better inspection and cleaning of the annular space 52. Moreover, the connector vent openings 56 and the cap vent openings 80, in combination with the annular space 52, form a continuous passageway (see FIG. 9) for airflow to enter the annular space at one end and exit the other end for enhanced drying and to prevent an airlock that might restrict airflow in and out of the annular space. As such, as used herein reference to connector outer-housing vent openings being "at the outer-housing endwall" includes the vent opening being formed in or by the outer-housing endwall 50 as well as being formed in or by the outer-housing sidewall 48 but immediately adjacent the outer-housing endwall to provide the continuous airflow passageway along substantially the entire length of the annular space 52.

In addition, to make sure that the cap vent openings 80 are at least partially exposed and uncovered (sufficiently for functioning for their intended purpose as described herein) when the cap 70 is in the plugged position on the connector 30, engaging stop surfaces 58 and 82 can be provided on the connector and the cap, respectively, to define (and thus limit) the how far the cap fits onto the connector. In the depicted embodiment, for example, the connector stop surface 58 is formed by a rim of the connector plug 44 defining the lumen 40, and the cap stop surface 82 is formed by a base of the cap plug 76. As can be seen for example in FIGS. 8-9, in the plugged position the cap vent openings 80 are partially covered but still partially exposed to permit fluid flow therethrough. Alternatively, the connector and cap stop surfaces can be formed by at least one inward-extending member (e.g., a collar, flange, rib, tab, or the like) of the outer-housing sidewall and by the rear (insertion) ends of the cap sidewall segments, respectively, so the inward-extending members limit how far into the annular space the cap sidewall segments can be inserted. Further alternatively, the connector stop surface can be in the form of an endwall, collar, flange, rib, tab, or the like on or adjacent the connector plug and/or lumen (e.g., within the lumen), and/or the cap stop surface can be in the form of a skirt, collar, flange, rib, tab, wing, or the like on or adjacent the cap plug.

It should be noted that the depicted embodiment includes the connector vent openings 56 and the cap vent openings 80 in combination, while other embodiments include only one of these two features. Furthermore, it should be noted that some embodiments include connector vent openings in the outer-housing sidewall as an addition or alternate to the depicted connector vent openings 56 in the outer-housing endwall 48, while other embodiments include cap vent openings in the cap endwall as an addition or alternate to the depicted cap vent openings 80 in the cap sidewall 78. As such, any of the vent openings disclosed herein can be implemented individually or in any combination with any other vent opening(s) disclosed herein or not disclosed herein.

Figure 10:
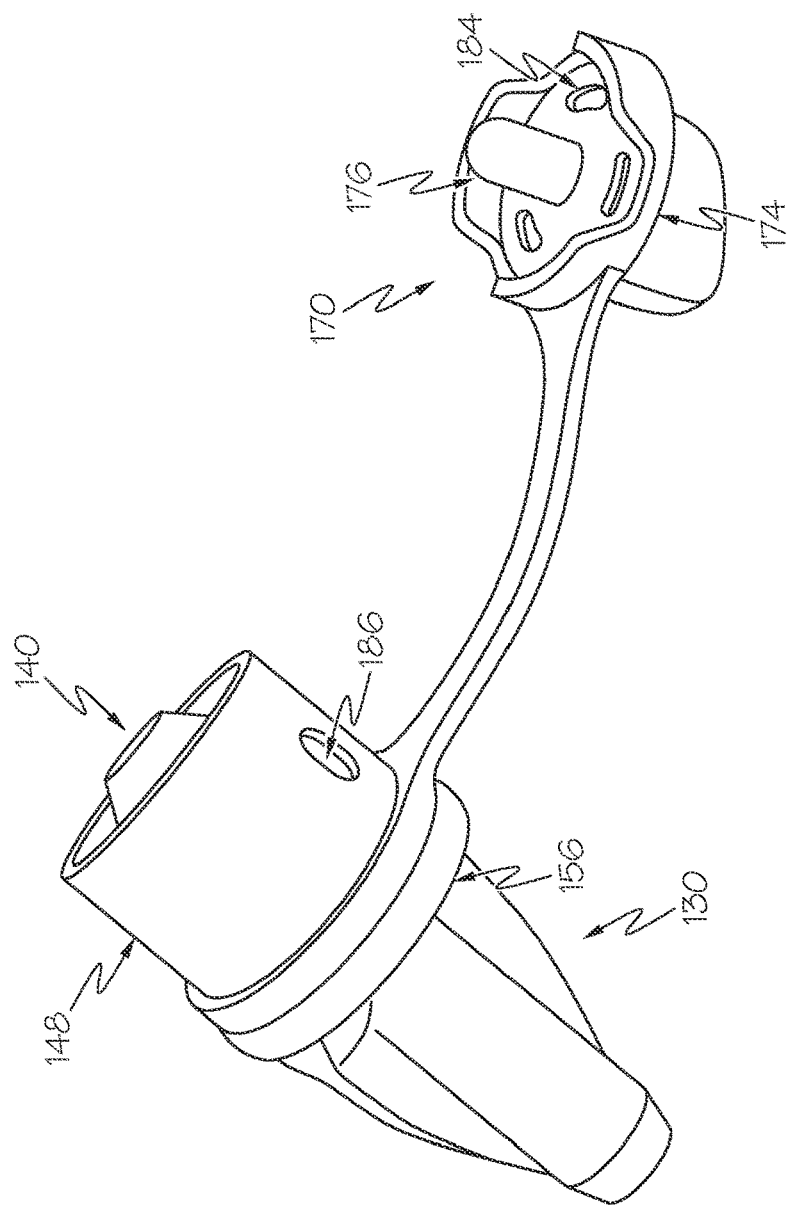
FIG. 10 is a perspective view of a vented connector according to a second example embodiment, shown with its cap unplugged so that it's ready for connection to a mating female connector.

FIG. 10 shows a vented connector 130 according to a second example embodiment of the present invention. The vented connector 130 is substantially similar to that of the first example embodiment described above, with exceptions as noted herein. In this embodiment, for example, the connector 130 includes one or more vent openings 186 formed in the outer-housing sidewall 148, in addition to the one or more vent openings 156 formed in the outer-housing endwall (not shown) described above. The connector vent openings 186 in the outer-housing sidewall 148 provide for drainage and drying, vacuum breaking, and enhanced inspection and cleaning similarly to the venting in the first example embodiment.

In the depicted embodiment, the connector vent openings 186 are generally circular in shape, though in other embodiments the vent openings can have an oval, polygonal, conical, or other regular or irregular shape. The depicted connector vent openings 186 are positioned sufficiently away from the front/cooperating connector end of the connector 130 that they are not blocked by the cap sidewall segments when the cap 170 is plugged onto the connector (with the cooperating connector detached). In other embodiments, the vent openings are provided with deflectors (e.g., V-shaped members extending inward from the inner surface of the outer-housing sidewall and positioned between the vent openings and the front end) that are engaged by and induce rotation of the cap sidewall segments when the cap is plugged onto the connector so that the vent openings align with the cap sidewall vent openings. And in still other embodiments, an array or series of the sidewall vent openings are provided.

In addition, the cap 170 can have one or more vent openings 184 axially formed in the cap body or endwall 174. The cap vent openings 184 are positioned radially outward from the cap plug 176 so that when the cap 170 is plugged onto the connector 130 they provide ventilation to the annular space 152 but they do not provide ventilation to the lumen 140. The cap vent openings 184 can be in the form of curved slots (as depicted) or they can have a circular, polygonal, conical, or other regular or irregular shape. In other embodiments, the connector 120 includes only the cap vent openings 184 or only the connector vent openings 186.

Figure 11:
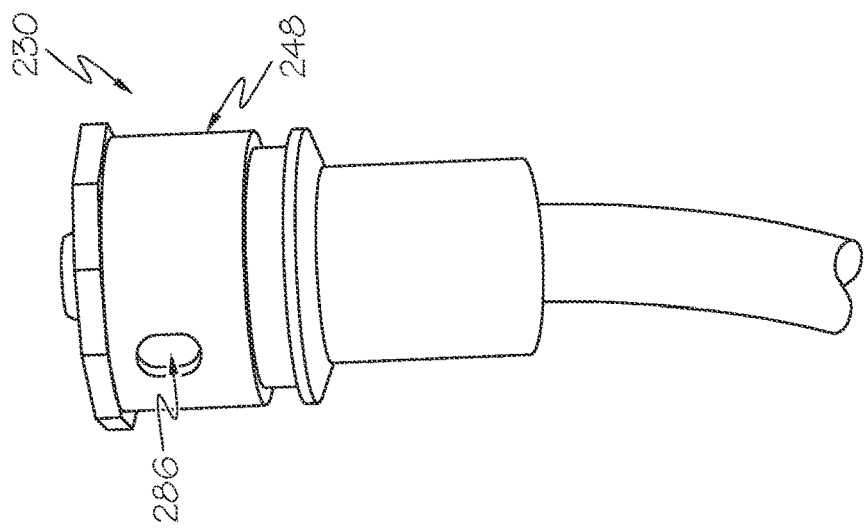
FIG. 11 is a perspective view of a vented connector according to a third example embodiment, shown without its cap.

FIG. 11 shows a vented connector 230 according to a third example embodiment of the present invention. The vented connector 230 is substantially similar to those of the first and second example embodiments described above, with exceptions as noted herein. In this embodiment, for example, the connector 230 includes the one or more vent openings 286 formed in the outer-housing sidewall 248, but not any vent openings formed in the outer-housing endwall. The connector vent openings 286 in the outer-housing sidewall 148 provide for drainage and drying, vacuum breaking, and enhanced inspection and cleaning similarly to the venting in the first and second example embodiments. It should be noted that the connector 230 is depicted without a cap, though in some embodiments a cap is provided, and the cap can include cap vent openings as described herein as an addition or alternate to the connector vent openings 286.

As described above, the cap comprises a plug that is configured for sealing off the lumen of the connector from outside contamination. In example embodiments, the plug is generally substantially cylindrical with a generally uniform outer periphery having a generally consistent outer diameter. According to example embodiments, the plug is configured such that interference with the lumen occurs when the plug is fully inserted therein or for example within about 1 millimeter from being fully inserted. According to example embodiments, the lumen comprises a diameter of about 2.90 millimeters.

FIGS. 12-15 show a cap 300 according to another example embodiment of the present invention. In example embodiments, the cap 300 is substantially similar to the caps as described above, for example, comprising a body 310, a sidewall 320, and one or more vent openings 350 defined by gaps in the sidewall 320. In addition, the cap 300 has a tether 340 extending from the cap body 310. In example embodiments, the cap body 310 further comprises an upper surface 312 from which a handle 330 extends (e.g., for gripping) and a lower surface 314 from which a plug 360 extends. In example embodiments, the plug 360 comprises one or more projections, ribs or other surface features 380 provided thereon, for example, to provide for an interference fit with the lumen of the male connector (see FIG. 15).

Figure 14:
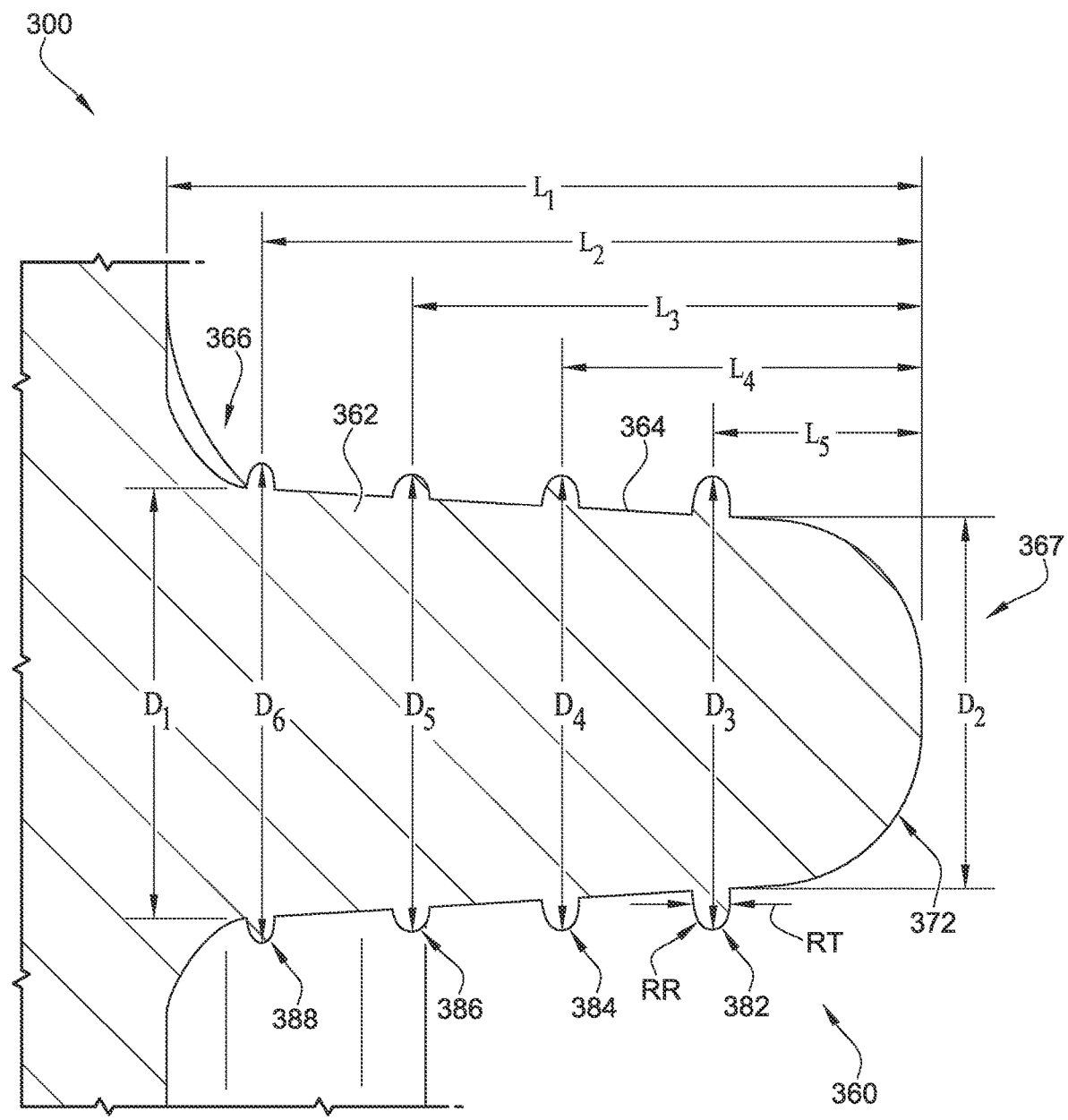
FIG. 14 detailed view of a portion of the tethered plug of FIG. 13.

As depicted in FIG. 13, the plug 360 axially extends along an elongate axis X between a first end 366 (generally adjacent and abutting the lower surface 314) and a second end 367 to define a length L1 therebetween (see FIG. 14). In example embodiments, the plug 360 comprises a cylindrical body 362 and an outer peripheral surface 364. According to example embodiments, the body 362 is not entirely cylindrical, for example, wherein an angle a is defined between the elongate axis X and the outer periphery 364 of the plug 360. According to example embodiments, the plug 360 comprises at least some taper thereto, for example, wherein the angle a is generally between about 0.5-20 degrees, for example between about 7-15 degrees according to one example embodiment. In one example embodiment, a first radiused transition is provided where the lower surface 314 and the first end 366 abut or engage each other, and a second radiused transition 372 is provided for extending between the outer surface 364 and the second end 367. According to example embodiments, the plug 360 is generally integrally formed with the lower surface 314 of the cap 300. However, according to other example embodiments, the plug 360 can be movably mounted thereto, or can be a separate piece that is generally movably mounted or removably mountable to the lower surface 314.

Figure 15:
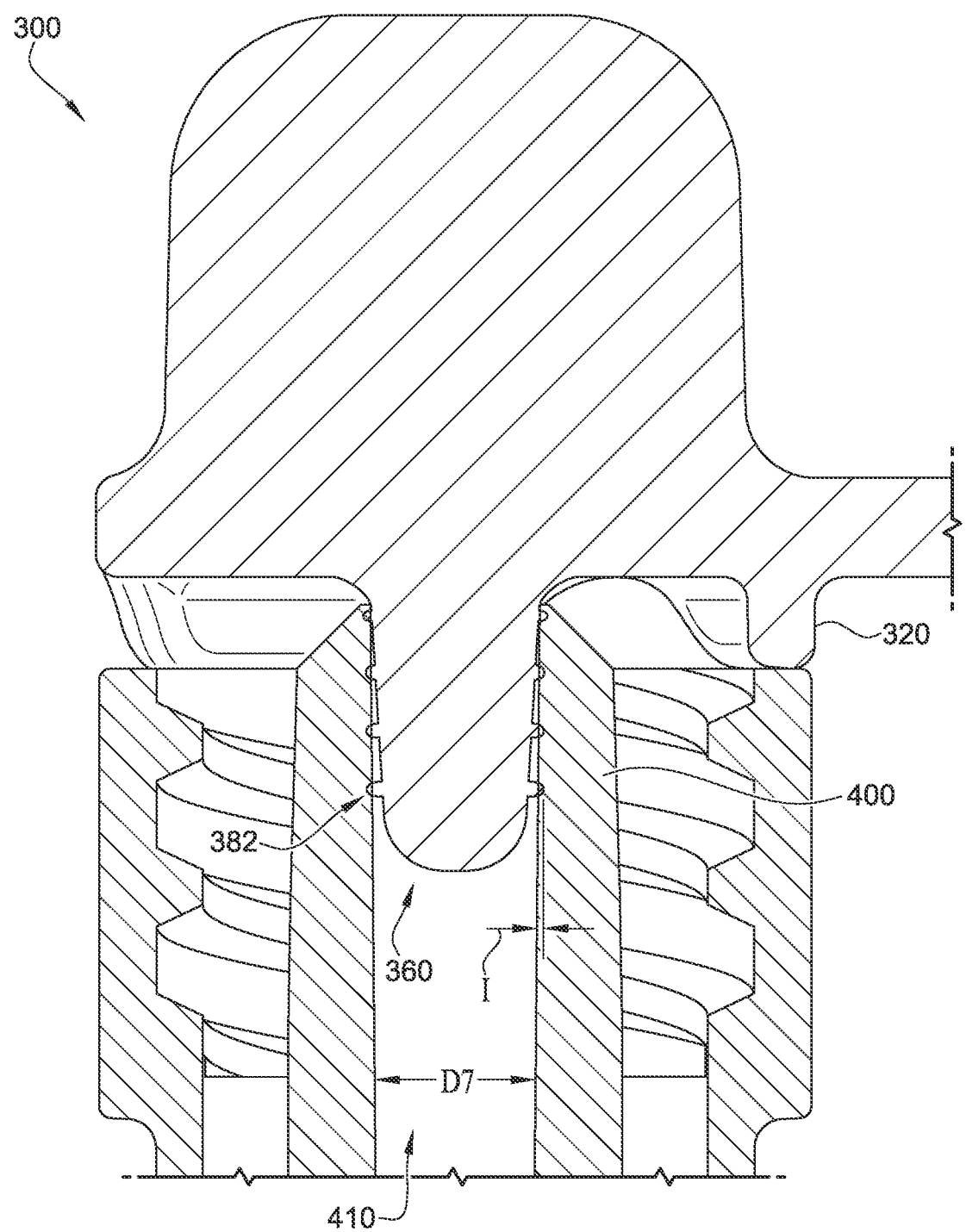
FIG. 15 is a cross-sectional view of the tethered plug of FIG. 13 connected and plugging the lumen of a male connector.

In example embodiments, one or more ribs, sealing features or projections 380 are provided on the outer surface 364 of the plug body 362, for example, which generally extends outwardly therefrom and around the entire periphery thereof to define a generally raised abutment or seal ring for engagement with the lumen 410 of the male connector 400 (see FIG. 15). As such, the outermost periphery or outer surface of the one or more projections 380 provides for an interference fit with the lumen 410 of the male connector 400. In example embodiments, the plug 360 comprises an array of about four spaced-apart projections 380 positioned along the length L1, for example, wherein each projection 380 generally extends around the entirety of the outer surface 364 of the plug body 362.

As depicted in FIG. 14, the plug 360 comprises a first projection 382 near the second end 367, a second projection 384 spaced apart from the first projection 382, a third projection 386 spaced apart from the second projection 384, and a fourth projection 388 spaced apart from the third projection 386. In example embodiments, each of the projections 382, 384, 386, 388 extend around the entirety of the plug body 360, and thus, insertion within the lumen provides at least four separate sealing surfaces wherein outer surfaces of the projections engage with the interior surface of the lumen 410 (see FIG. 15). In example embodiments, only one, two or three, or more than four projections can be provided on the plug 360 so as to provide interference with the lumen 410 of the male connector 400, for example, so as to provide at least one seal between at least a portion of the projection and the interior surface of the lumen 410.

According to the depicted example embodiment of FIG. 14, the projections 382, 384, 386, 388 define a thickness RT and an outer major radius RR. According to one example embodiment, the thickness RT of the projection 382 is about 0.250 millimeters and the radius RR is about 0.266 millimeters. According to example embodiments, the thickness and radius of the projection 382 (or the other projections 384, 386, 388) can be chosen as desired, for example, at least between a thickness of between about 0.095-2.5 millimeters and a radius of between about 0.075-1.5 millimeters. Optionally, according to other example embodiments, the thickness and radius can be chosen as desired. In alternate example embodiments, one or more of the projections can be provided with various other projections, ribs, tabs or other sealing features or elements in various sizes and shapes, for example, so as to be configured to allow for a desired about of interference or engagement with the interior surface of the lumen 410. For example, according to example embodiments, the projections are preferably configured so as to provide a desirable pull or removal force, for example, such that at least a minimum amount of force is required to disengage the plug from the lumen. In example embodiments, the removal force is generally configured to be between about 2.5-15 newtons (N). In example embodiments, the plug 360 (and projections 382, 384, 386, 388) generally provide for an interference fit such that a removal force of 6-8 newtons. In other example embodiments, the interference fit is such that continuous insertion and removal of the plug from the lumen at least provides for a removal force of about 2.5 N.

As described above, the plug 360 extends a length L1 between the lower surface 314 and the second end 367. In example embodiments, the length L1 is generally between about 2.25-8.50 millimeters, more preferably between about 4-7 millimeters, for example about 5.03 millimeters according to one example embodiment. The plug comprises a first outer diameter D1 that is generally near the first end 366 and a second outer diameter D2 that is generally near the first projection 382. According to one example embodiment, the first outer diameter D1 is about 2.871 millimeters and the second outer diameter D2 is about 2.478 millimeters, for example, such that at least some taper is provided along the length of the plug body 362 (e.g., defined by angle α). According to one example embodiment, the angle α is about 3.5 degrees. Accordingly, the entire angle between opposite sides of the outer surface 364 is about 7 degrees according to one example embodiment. According to another example embodiment, the angle α is between about 4-8 degrees. According to another example embodiment, the angle α can be chosen as desired, for example, between about 0.25 degrees to about 16 degrees.

According to example embodiments, the first projection 382 is generally spaced a length L5 of about 1.389 millimeters from the second end 367 and comprises an outer diameter D3 of about 3.024 millimeters. The second projection 384 is generally spaced a length L4 of about 2.392 millimeters from the second end 367 and comprises an outer diameter D4 of about 3.034 millimeters. The third projection 386 is generally spaced a length L3 of about 3.392 millimeters from the second end 367 and comprises an outer diameter D5 of about 3.051 millimeters. The fourth projection 388 is generally spaced a length L2 of about 4.392 millimeters from the second end 367 and comprises an outer diameter D6 of about 3.20 millimeters.

According to example embodiments, the diameters, lengths, radii or other dimensions of the plug can preferably be varied as desired, for example, so as to provide a desired interference fit with the lumen of the male connector while providing a desired removal force. According to example embodiments, the dimensions as described above can preferably comprise tolerances up to about 0.10 millimeters. Thus, according to some example embodiments, the diameters, lengths or other dimensions of the plug as described above can preferably vary at least by ±0.10 millimeters. According to other example embodiments, the dimensions can be chosen as desired.

According to example embodiments (as described above), the one or more projections can preferably comprise a desired amount of interference I with the lumen 410. For example, as depicted in FIG. 15, the first projection 382 defines the interference I provided between the lumen 410. According to one example embodiment, with the lumen comprising an inner diameter D7 of about 2.90 millimeters and with the first projection 382 comprising a diameter D3 of about 3.024 millimeters, the interference I provided between the first projection 382 and the lumen 410 is about 0.062 millimeters. According to other example embodiments, the interference I can be between about 0.0125-0.350 millimeters, for example between about 0.040-0.180 millimeters according to one example embodiment.

According to the depicted example embodiment, the second projection 384 comprises an interference I of about 0.067 millimeters (D4=3.034 mm and D7=2.90 mm), the third projection 386 comprises an interference I of about 0.076 millimeters (D5=3.051 mm and D7=2.90 mm), and the fourth projection 388 comprises an interference I of about 0.150 millimeters (D6=3.20 mm and D7=2.90 mm). Thus, according to one example embodiment, the fourth projection 388 comprises greater interference with the lumen 410 than the third projection 386, the third projection comprises greater interference with the lumen 410 than the second projection 384, and the second projection comprises greater interference with the lumen 410 than the first projection 382. Optionally, according to other example embodiments, the projections can be dimensioned to provide a desired amount of interference with the lumen.

Figure 16:
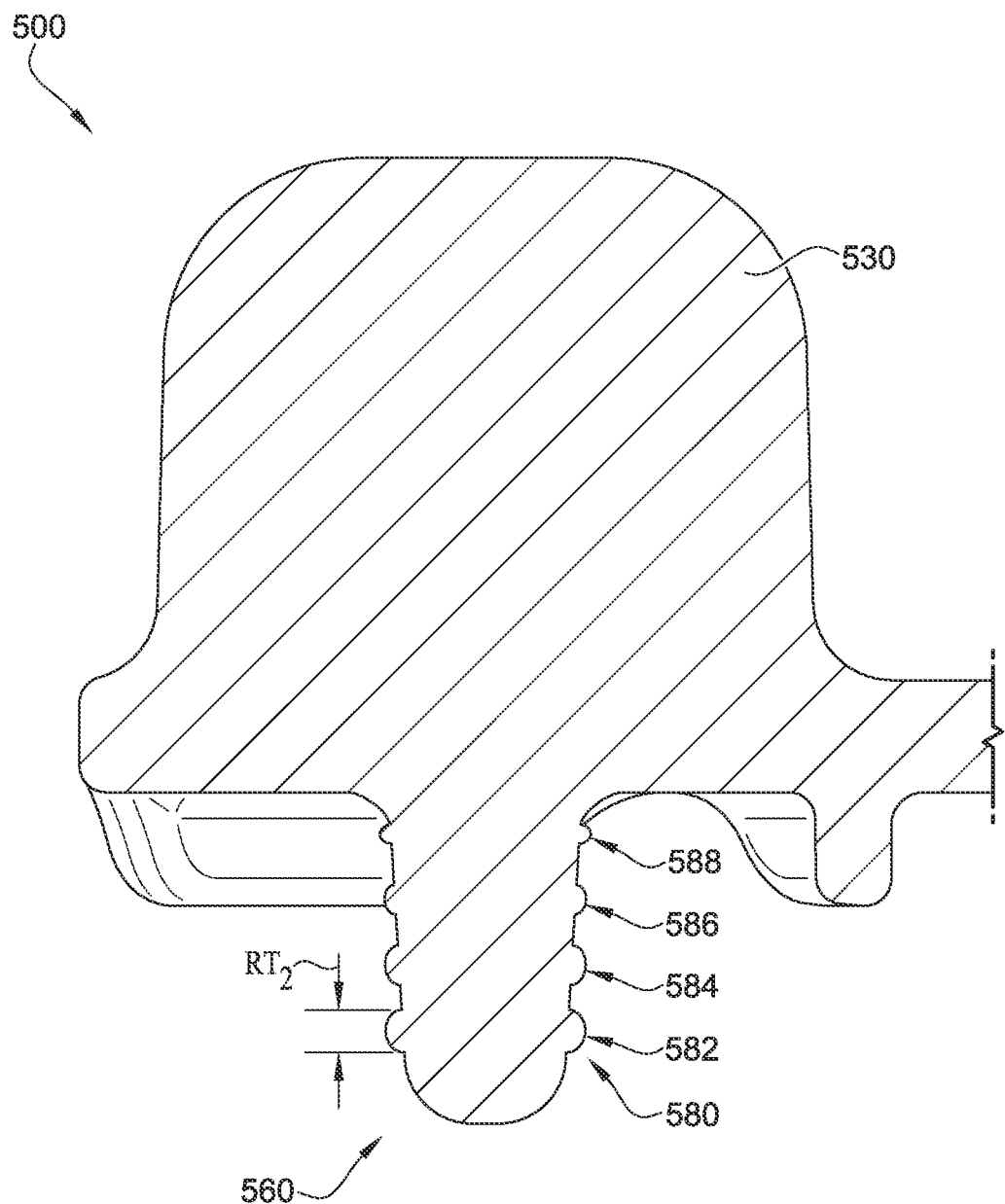
FIG. 16 shows a cross-sectional view of a tethered plug according to another example embodiment of the present invention.

According to another example embodiment, the projections 382, 384, 386, 388 can be thickened such that the width thereof is increased while generally keeping the outer diameters the same. For example, the cap 500 as depicted in FIG. 16 comprises a plug 560 comprising a plurality of projections 580 as is described above with respect to the cap 300. In example embodiments, the projections 582, 584, 586, 588 comprise substantially similar diameters in comparison to the projections 382, 384, 386, 388 of the plug 360. However, the first projection 582 comprises a thickness RT2 of about 0.650 millimeters, for example, about 0.400 millimeters greater than the thickness RT of the projection 382. In example embodiments and in a similar manner as described above, the second projection 584 comprises a thickness that is about 0.300 millimeters greater than the thickness of the projection 384, the third projection 586 comprises a thickness that is about 0.200 millimeters greater than the thickness of the projection 386, and the fourth projection 588 comprises a thickness that is about 0.100 millimeters greater than the thickness of the projection 388.

Figure 17:
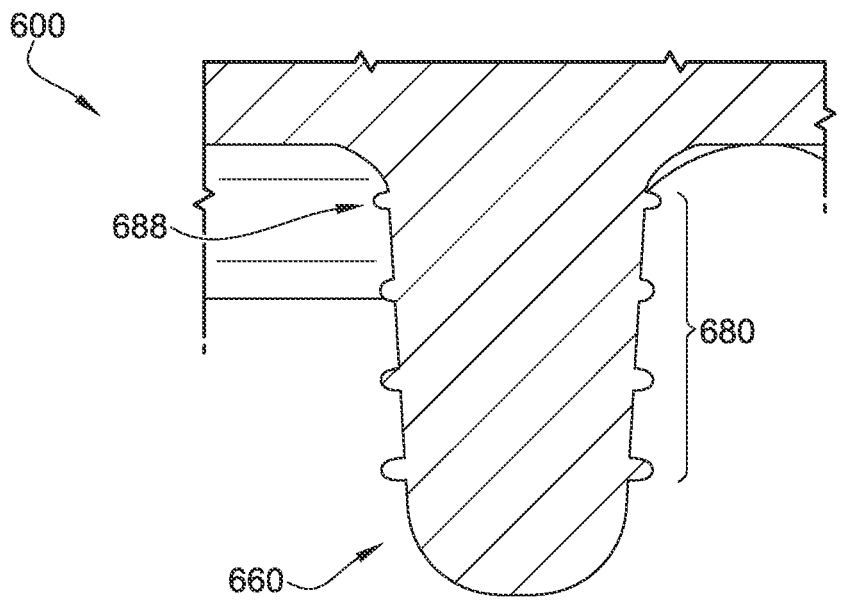
FIGS. 17-18 show an assembly view of a tethered plug and male connector according to another example embodiment of the present invention, the plug having one or more projections thereon and the male connector defining a lumen extending therethrough wherein one or more undercuts or receivers are provided for receiving one or more projections of the tethered plug.
Figure 18:
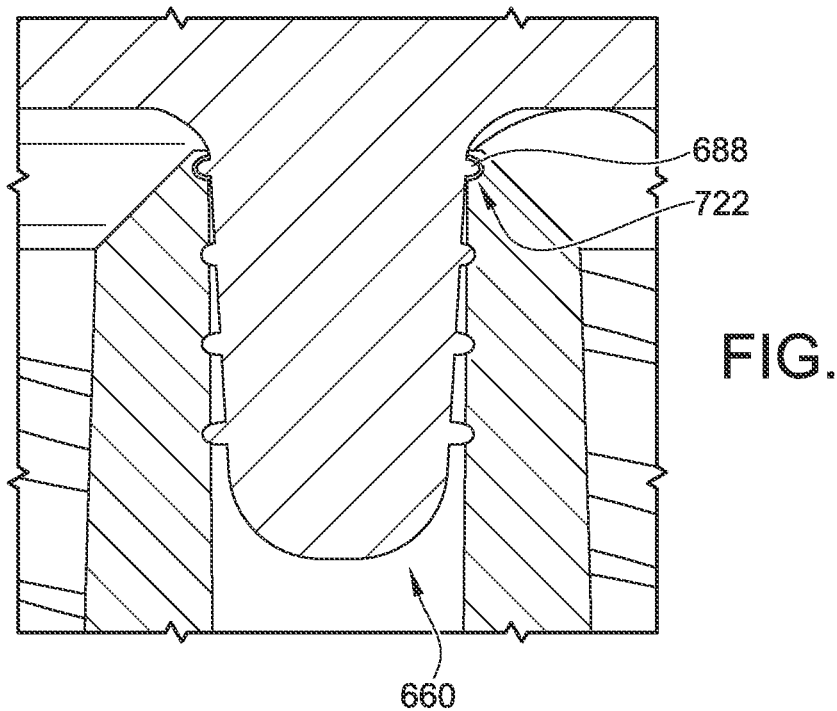

According to yet another example embodiment of the present invention, an annular recess or undercut can be provided with a portion of the lumen or male connector, for example, so as to provide for engagement with one or more projections of the plug. For example, as depicted in FIGS. 17-18, a cap 600 comprising a plug 360 and one or more projections 680 is provided for sealing engagement within a lumen 710 of a male connector 700. In example embodiments, an internal surface 720 that is defined within the lumen 710 comprises an annular undercut or recess 722 to provide for engagement with the fourth projection 688. In example embodiments, the undercut 722 is generally shaped similarly to the profile of the projection 688, or for example, can be shaped as desired to provide for at least some interference or engagement when the plug is fully inserted within the lumen 710. According to some example embodiments, the undercut 722 is at least slightly larger than the profile of the projection 688 so as to provide minimal interference when the plug 660 is seated within the lumen 710. However, upon removal or insertion, the projection 688 must overcome the engagement or interference with the entrance of the undercut 722 and along the internal surface 720. Accordingly, while the undercut 722 can be configured to have substantially small amounts of interference when the plug is fully inserted, insertion and removal of the plug can be configured so as to provide a desired removal force, for example, such that the plug is not unintentionally removed causing unintentional exposure of the lumen 710 to the elements.

According to some example embodiments, the undercut can be configured so as to provide less resistance when the plug is fully inserted and rotating about the lumen 710. In some example embodiments, the plug can comprise one or more projections intended for an interference fit with the internal surface 720 of the lumen 710 and one or more projections intended for seating within one or more undercuts provided within the lumen 710. In this manner, the amount of interference can be chosen as desired so as to provide a sufficient seal and a desired removal force. Furthermore, the amount of interference can be chosen as desired to additional provide for at least some rotational movement of the plug relative to the lumen 710 while maintaining a desired removal force.

According to example embodiments, the cap (and plug thereof) in addition to the connector and the hub of the lumen can be formed from any desirable material including plastics, thermoplastics, polymers, or other desirable materials. In example embodiments, the cap (and plug thereof) is formed from a polyvinyl chloride material. Optionally, other materials may be chosen as desired. According to example embodiments, the male connector and lumen thereof can be formed from a polymer material including polypropylene (PP), acrylonitrile butadiene styrene (ABS), or thermoplastic polyurethane (TPU). In additional example embodiments, the cap, plug, projections, male connector or lumen thereof can preferably be formed from any available desired material (or a combination of two or more materials).

While the invention has been described with reference to preferred and example embodiments, it will be understood by those skilled in the art that a variety of modifications, additions and deletions are within the scope of the invention, as defined by the following claims.

What is claimed is:

1. A connector for connection to a fluid vessel and to a cooperating connector, the connector comprising:
    a first end configured to attach to the fluid vessel, a second end coaxial with the first end, and a lumen extending through the connector from the first end to the second end;
    a fluid-seal fitting that at least partially defines the lumen and is configured to sealingly mate with the cooperating connector to provide conveyance of a fluid;
    an outer housing positioned around the fluid-seal fitting to form an annular space therebetween with an access opening at the second end of the connector, wherein the outer housing comprises a sidewall arranged coaxially with the fluid-seal fitting and the access opening, the outer housing having at least one connector vent opening configured to provide fluid communication between the annular space and an environment external to the annular space; and
    a cap repositionable between a plugged position capping the second end of the connector and an unplugged position not capping the second end of the connector, the cap including one or more cap vent openings, wherein the at least one connector vent opening, the one or more cap vent openings, and the annular space form a continuous passageway, wherein the continuous passageway provides fluid communication from the one or more cap vent openings to the annular space and to the environment external to the annular space through the at least one connector vent opening when the cap is in the plugged position capping the access opening of the annular space, wherein the one or more cap vent openings allow for drainage and air-drying of any residual amount of fluid in the annular space,
    wherein the cap further comprises a plug for providing sealed engagement with the lumen, the plug comprising an elongate body extending from a first end to a second end, an outer peripheral surface, and at least one projection extending around the outer peripheral surface of the plug, the at least one projection providing for an interference fit with an internal surface of the lumen to seal the lumen from outside contamination.

2. The connector of claim 1, wherein the plug tapers from the first end to the second end.

3. The connector of claim 1, wherein the plug comprises a length of about 5 millimeters.

4. The connector of claim 1, wherein the at least one projection comprises a rib-like ring projecting around an entire periphery of the outer peripheral surface of the plug, and wherein an outer surface of the rib-like ring is configured for providing the interference fit with the internal surface of the lumen of the fluid-seal fitting.

5. The connector of claim 1, wherein the at least one projection comprises two or more projections.

6. The connector of claim 5, wherein each projection has a thickness that is unequal to the thickness of any other of the projections.

7. The connector of claim 6, wherein each projection has a diameter along the elongate body that is unequal to the diameter of each other projection.

8. The connector of claim 5, wherein each of the projections are equally spaced apart from each other along the elongate body of the plug.

9. The connector of claim 1, wherein the at least one projection of the plug comprises four spaced-apart projections, each of the projections extending around an entire periphery of the plug.

10. The connector of claim 1, wherein the at least one projection comprises an outer diameter of between about 3.0-3.5 millimeters and wherein an internal diameter of the lumen is about 2.90 millimeters.

11. The connector of claim 10, wherein between about 0.040-0.180 millimeters of interference is provided between the at least one projection and the internal surface of the lumen.

12. The connector of claim 11, wherein the interference fit between the at least one projection and the internal surface of the lumen is such that a removal force of between about 2.5-15 N is required to remove the fully-inserted plug from the lumen.

13. The connector of claim 1, wherein at least a portion of the lumen comprises a recessed portion or an annular undercut defined therein configured for receiving the at least one projection of the plug of the cap.

14. The connector of claim 1, the outer housing further comprising an endwall extending between the sidewall and the fluid-seal fitting.

15. The connector of claim 14, further comprising one or more vent openings extending through the endwall of the outer housing.

16. A connector for connection to a fluid vessel and to a cooperating connector, the connector comprising:
a first end configured to attach to the fluid vessel, a second end, and a lumen extending through the connector from the first end to the second end;
a fluid-seal fitting that at least partially defines the lumen and is configured to sealingly mate with the cooperating connector to provide conveyance of a fluid;
an outer housing positioned around the fluid-seal fitting, the outer housing having a sidewall arranged coaxial with the fluid-seal fitting, wherein an annular space is defined between the fluid-seal fitting and the sidewall of the outer housing and is orientated coaxially with the fluid-seal fitting, wherein an access opening is defined at the second end of the connector and wherein the outer housing has a connector vent opening in fluid communication with the annular space to provide fluid communication to an environment external to the annular space; and
a cap repositionable between a plugged position capping the second end of the connector and an unplugged position not capping the second end of the connector, the cap including a cap vent opening, wherein the connector vent opening, the cap vent opening, and the annular space form a continuous passageway, wherein the continuous passageway provides fluid communication from the cap vent opening to the annular space and to the environment external to the annular space through the connector vent opening when the cap is in the plugged position capping the access opening of the annular space, wherein the cap vent opening allows for drainage and air-drying of any residual amount of fluid in the annular space.

17. A connector for connection to a fluid vessel and to a cooperating connector, the connector comprising:
a first end configured to attach to the fluid vessel, a second end, and a lumen extending through the connector from the first end to the second end;
a fluid-seal fitting that at least partially defines the lumen and is configured to sealingly mate with the cooperating connector to provide conveyance of a fluid;
an outer housing positioned around the fluid-seal fitting, the outer housing having a sidewall arranged coaxial with the fluid-seal fitting and having an endwall, wherein an annular space is defined between the fluid-seal fitting and the sidewall of the outer housing and is orientated coaxially with the fluid-seal fitting, wherein an access opening is defined at the second end of the connector opposite the endwall and wherein the outer housing has a connector vent opening in fluid communication with the annular space to provide fluid communication to an environment external to the annular space; and
a cap repositionable between a plugged position capping the second end of the connector and an unplugged position not capping the second end of the connector, the cap including a body, a peripheral sidewall extending from the body, and a cap vent opening formed in the peripheral sidewall,
wherein the peripheral sidewall of the cap is configured to be received within the annular space through the access opening when the cap is in the plugged position,
wherein the cap vent opening extends beyond the endwall of the outer housing to form a continuous passageway between the connector vent opening, the cap vent opening, and the annular space.

* * * * *

UNITED STATES PATENT AND TRADEMARK OFFICE
CERTIFICATE OF CORRECTION

Page 1 of 1

PATENT NO. : 12,233,231 B2
APPLICATION NO. : 17/743558
DATED : February 25, 2025
INVENTOR(S) : Aaron N. Ingram et al.

It is certified that error appears in the above-identified patent and that said Letters Patent is hereby corrected as shown below:

In the Claims

Column 15, Line 6:
In Claim 2, after "end" insert -- of the plug --.

Column 15, Line 6:
In Claim 2, delete "end." and insert -- end of the plug. --.

Signed and Sealed this
Twenty-seventh Day of May, 2025

Coke Morgan Stewart
*Acting Director of the United States Patent and Trademark Office*